US007238810B2

(12) United States Patent
Bhatarah et al.

(10) Patent No.: US 7,238,810 B2
(45) Date of Patent: Jul. 3, 2007

(54) PREPARATION OF CABERGOLINE

(76) Inventors: Parveen Bhatarah, Resolution Chemicals Ltd., Wedgwood Way, Stevenage, Herts (GB) SG1 4QT; Derek McHattie, Resolution Chemicals Ltd., Wedgwood Way, Stevenage, Herts (GB) SG1 4QT; Alan Greenwood, Resolution Chemicals Ltd., Wedgwood Way, Stevenage, Herts (GB) SG1 4QT; Paul Christopher Marcus Hedger, Resolution Chemicals Ltd., Wedgwood Way, Stevenage, Herts (GB) SG1 4QT ( * ) Notice: Subject to any disclaimer, the term of this patent is extended or adjusted under 35 U.S.C. 154(b) by 225 days.

(21) Appl. No.: 11/100,934

(22) Filed: Apr. 7, 2005

(65) Prior Publication Data

US 2006/0217555 A1   Sep. 28, 2006

(51) Int. Cl.
*C07D 457/06*   (2006.01)
*C07D 457/02*   (2006.01)

(52) U.S. Cl. ......................................... 546/69; 546/67

(58) Field of Classification Search .................. 546/69, 546/67
See application file for complete search history.

(56) References Cited

U.S. PATENT DOCUMENTS

| 3,920,664 | A | 11/1975 | Clemens et al. |
| 4,180,582 | A | 12/1979 | Kornfeld et al. |
| 4,202,979 | A | 5/1980 | Kornfeld et al. |
| 4,229,451 | A | 10/1980 | Fehr et al. |
| 4,246,265 | A | 1/1981 | Kornfeld et al. |
| 4,526,892 | A | 7/1985 | Salvati et al. |
| 4,675,404 | A | 6/1987 | Barnardi et al. |
| 4,782,152 | A | 11/1988 | Misner |
| 5,382,669 | A | 1/1995 | Candiani et al. |
| 6,395,901 | B1 | 5/2002 | Mangia et al. |

FOREIGN PATENT DOCUMENTS

| CH | 535235 | | 3/1973 |
| CH | 535236 | | 3/1973 |
| CZ | 144634 | | 7/1972 |
| CZ | 287176 | | 4/1999 |
| FR | 2479829 | | 10/1981 |
| GB | 1451724 | | 10/1976 |
| GB | 1499420 | | 2/1978 |
| GB | 2014140 | A | 8/1979 |
| GB | 2103603 | A | 2/1983 |
| GB | 0409785-3 | | 4/2004 |
| WO | WO 01/70740 | A1 | 9/2001 |
| WO | WO 01/72746 | A1 | 10/2001 |
| WO | WO 01/72747 | A1 | 10/2001 |
| WO | WO 03/078392 | A2 | 9/2003 |
| WO | WO 03/078433 | A1 | 9/2003 |
| WO | WO 2004/101510 | A2 | 11/2004 |

OTHER PUBLICATIONS

I. Candiani, W. Cabri, F. Zarini, A. Bedeschi and S. Penco, Synlett, The Ligand Effect in Copper (I)—Catalyzed Chemoselective Amide . . . , (1995), 605-606.

Sabatino, Sanseverino and Tonani, X-Ray Crystal Structure and Conformation Analysis of [Cabergoline]. . . , II Farmaco, 50(3), (1995), 175-178.

E. Brambilla, E. di Salle, G. Briatico, S. Mantegani and A. Temperilli, Synthesis and Nidation Inhibitory Activity . . . , New Eur. J. Med. Chem., 24, (1989), 421-426.

S. Montegani, E. Brambilla and A. Ermoli, Synthesis of Tritium and Carbon-14 labeled N . . . , J. Labelled Compd. Radiopharm., vol. 29, No. 5., 519-533, (1991).

S Ohno, Y. Adachi, M. Koumori, K. Mizukoshi, M. Nagasaka, K. Ichihara and El Kato, Synthesis and Structure . . . , Chem. Pharm. Bull., 42(7), vol. 42, No. 7, (1994), 1463-1473.

R. Battaglia, M. Strolin Benedetti, S. Mantegani, M.G. Castelli, G. Castelli, G. Cocchiara and P. Dostert, Disposition . . . , Xenobiotica, vol. 23, No. 12, (1993), 1377-1389.

J. Benes, A. Cerny, V. Miller and S. Kudrnac, Epimerization of Esters of Stereoisomeric . . . , Coll. Czech. Chem. Commun., vol. 48, (1983), 1333-1340.

A. Stoll and A. Hofman, Die Dihydroderivate der rechtsdrehenden . . . , Helv. Chim. Acta, vol. 29, Fasc. 3, (1946), 635-653.

P.S. Stadler, Eine einfache Veresterungsmethode im Eintopf-Verfahren, Helv. Chim. Acta, vol. 61, Fasc. 5, (1978), 1675-1681.

T. Fehr, P. Stadler and A. Hofman, Demethylierung des Lysergsauregerustes, Helv. Chim. Acta, 53, Fasc. 8, (1970), 2197-2201.

J. Krepelka, A. Cerny, R. Kotva and M. Semonsky, Some 6-Alkyl Derivatives of D-8-Cyanomethyl . . . , Coll. Czech. Chem. Commun., vol. 42, (1977), 1209-1215.

W.A. Jacobs and L.C. Craig, Isomeric Dihydrolysergic Acids and the Structure of Lysergic Acid, J. Biol. Chem., (1936), 227-239.

A. Cerney and M. Semonsky, Mutterkornalkaloide, Pharmazie, vol. 26(12), (1971), 740-741.

E.C. Kornfeld, E. J. Fornefeld, G. B. Kline, M. J. Mann, R. G. Jones and R. B. Woodward, The Total Synthesis of Lysergic Acid, J. Am. Chem. Soc., (1956), 3087-3114.

C.Z. Zhang, J.H. Yang, and J. Zhou, Zhongguo Yi Xue Ke Xue Yuan Xue Bao, vol. 6, No. 1, (1984), 70-72.

A. Kleeman, J. Engel, B. Kutscher, D. Reichert, Georg Thieme Verlag, Pharmaceutical Substances, 4th ed., 312-313, 2001.

C. Dollery and Churchill Livingstone, Therapeutic Drugs, 2nd ed., (1999), C1-C4.

K. Parfitt, The Pharmaceutical Press, Martindale, 32nd ed., (1999), 1135-1136.

(Continued)

*Primary Examiner*—Charanjit S. Aulakh
(74) *Attorney, Agent, or Firm*—Rakoczy Molino Mazzchi Siwik LLP

(57) ABSTRACT

A method of preparing cabergoline Form I, comprising forming a solvate including cabergoline and 4-fluorotoluene or 1,3,5-trimethylbenzene and obtaining cabergoline Form I from the solvate. Another aspect of the present invention provides a method for preparing cabergoline Form I comprising dissolving cabergoline in 4-fluorotoluene or 1,3,5-trimethylbenzene and recovering the cabergoline Form 1 polymorph. Cabergoline Form I can then be obtained from the solution, suitably by direct crystallization of Form I or by recovery of a solvate which can be converted to Form I.

68 Claims, 1 Drawing Sheet

OTHER PUBLICATIONS

M.D. Gottwald, J.L. Bainbridge, G.A. Dowling, M.J. Aminoff and B.K. Alldredge, Ann. Pharmacother., vol. 31, (1997), 1205-1217.

L.R. Wiseman and F. Fitton, Cabergoline—A Review of its Efficacy in the Treatment of Parkinson's Disease, CNS Drugs, vol. 12(6) (1999), 485-497.

K. Ichikawa and M. Kojima, Nippon Yakurigaku Zasshi, vol. 117, (2001), 395-400.

The Merck Index, 13th ed., (2001), 270.

V. Gotor, Non-Conventional Hydrolase Chemistry: Amide and Carbamate Bond Formation Catalyzed by Lipases, Bioorg. Med. Chem., vol. 7, (1999), 2189-2197.

A.M. Crider, R. Grubb, K.A. Bachmann and A.K. Rawat, Convenient Synthesis of 6-nor-9,10-dihydrolysergic Acid Methyl Ester, J. Pharm. Sci., vol. 70, No. 12, (1981), 1319-1321.

R.A. Olofson and J. Martz, A New Reagent for the Selective, High Yield N-Dealkylation of Tertiary Amines . . . , J. Org. Chem., vol. 49, (1984), 2081-2082.

R.A. Olofson and D.E. Abbott, Tests of a Piperidino Mask for the Protection of Functionalized Carbon Sites in Multistep Synthesis, J. Org. Chem., vol. 49, (1984), 2795-2799.

C. Allievi and P. Dostert, Quantitative Determination of Cabergoline in Human Plasma . . . , Rapid Commun. Mass Spectrom., vol. 12, (1998), 33-39.

V. Prelog, B.C. McKusick, J.R. Merchant, S. Julia and M. Wilhelm, Helv. Chim. Acta., vol. 39, (1956), 498-504.

J.R. Vaughan, Acylalkylcarbonates as Acylating Agents for the Synthesis of Peptides, J. Am. Soc., vol. 73, (1951), 3547.

E.R.H. Walker, The Functional Group Selectivity of Complex Hydride Reducing Agents, Chem. Soc. Rev., vol. 5, (1976), 23-51.

M.J. Kornet, P.A. Thio amd S.I. Tan, The Borane Reduction of Amido Esters, J. Org. Chem., vol. 33, No. 9, (1968), 3637-3639.

J.M. Lalancette, A. Freche, J.R. Brindle and M. Laliberte, Reductions of Functional Groups with Sulfurated Borohydrides. Synthesis, (1972), 526-532.

G. Cainelli, L. Caglioti and W. Barberi, Farmaco, Ed. Sci., vol. 22, No. 6, (1967), 456-462.

R.C. Larock, Comprehensive Organic Transflormations, 2nd ed., Wiley VCH, (1999), 1940-1977.

J.M. Humphrey and A.R. Chamberlin, Chemical Synthesis of Natural Product Peptides . . . , Chem. Rev., vol. 97, (1997), 2243-2266.

L.A. Carpino, A. Elfaham and F. Albericio, Racemization Studies During Solid-Phase Peptide Synthesis . . . , Tetrahedron Letters, vol. 35 (1994), 2279-2282.

J.C. Spetzler, M. Meldal, J. Felding, P. Vedso and M. Begtrup, Novel Acylation Catalysts in Peptide Synthesis . . . , J. Chem. Soc., Perkin Trans. vol. 1, (1998), 1727-1731.

F.S. Gibson, M.S. Park and H. Rapoport, Bis[[4-(2,2-dimethyl-1,3-dioxolyl)] methyl]-carbodiimide (BDDC) . . . , J. Org. Chem., vol. 59, (1994), 7503-7507.

F.S. Gibson and H. Rapoport, Carboxy Terminus Coupling Using 1,1'-Carbonylbis (3-methylimidazolium triflate) (CBMIT) . . . , J. Org. Chem., vol. 60, (1995), 2615-2617.

M. Soledad de Castro and J.V. Sinisterra-Gago, Lipase-Catalyzed Synthesis of Chiral Amides . . . , Tetrahedron, vol. 54, (1998), 2877-2892.

V.M. Sanchez, F. Rebolledo and V. Gotor, Candida Antarctica Lipase-Catalyzed Doubly Enantioselective Aminolysis Reactions . . . , J. Org. Chem., vol. 64, (1999), 1464-1470.

V.M. Stepanov, Proteinases as Catalysts in Peptide Synthesis, Pure and Appl. Chem., vol. 68, No. 6, (1996), 1335-1339.

G. Marzoni, W. Garbrecht, P. Fludzinski, and M. Cohen, 6-Methylergoline-8-carboxylic Acid Esters . . . , J. Med. Chem., vol. 30, (1987) 1823-1826.

US 7,238,810 B2

PREPARATION OF CABERGOLINE

This patent application claims priority to United Kingdom Patent Application No. GB 0505965.4, which was filed on Mar. 23, 2005. This UK application is hereby incorporated by reference in its entirety.

FIELD OF THE INVENTION

The present application relates to the preparation of cabergoline, in particular a new process for preparing cabergoline Form I.

BACKGROUND OF THE INVENTION

Cabergoline is an ergoline derivative with formula 1 ((6-allylergolin-8β-yl)-carbonyl)-1-(3-dimethylaminopropyl)-3-ethylurea. It is known for treatment of a number of diseases, including CNS disorders, reversible obstructive airways disease, prolactin inhibition, for controlling intraocular pressure and for treating glaucoma.

A number of different forms of cabergoline are known and, by way of example, PCT patent publication no. WO 01/72747 describes cabergoline Form II and PCT patent publication no. WO 01/72746 describes cabergoline Form VII.

Preparation of cabergoline Form I is described in PCT patent publication nos. WO 01/70740, WO 03/078392 and WO 03/078433. PCT patent publication no. WO 01/70740 teaches the preparation of crystalline Form I cabergoline from a solvent comprising a toluene/diethylether mixture whereas PCT patent publication nos. WO 03/078392 and WO 03/078433 teach crystalline cabergoline Form I that is obtained by drying a solvate of cabergoline and toluene.

Pending UK Patent Application No. GB 0409785-3 teaches a process for preparing cabergoline Form 1 in high yield and purity and with desirable particle size distribution using ethylbenzene optionally in conjunction with an antisolvent such as n-heptane. GB 0409785-3 further describes a cabergoline ethylbenzene solvate.

A series of cabergoline polymorphs are described in PCT patent publication no. WO 2004/101510.

It is desired in the present invention to prepare crystalline cabergoline of Form I having high purity. It is also desired to prepare cabergoline having a particle size (following crystallization) which is relatively small and which requires no or relatively little milling to obtain the particle size desired in the eventual pharmaceutical product. Milling and other such processing is undesirable as it tends to lead to conversion of pure polymorphic forms of cabergoline into polymorphic mixtures. One problem with the methods described in PCT patent publication no. WO 03/078433, for example, is that crystals of cabergoline Form I are obtained with a relatively large particle size.

It is also desired to provide a process for preparation of cabergoline in which conversion of an intermediate solvate to the final cabergoline Form I product is quick and efficient. A difficulty with known processes for this conversion is that protracted drying periods are required to remove the solvent from the solvate—in excess of 48 hours—for the methods set forth in PCT patent publication no. WO 03/078433.

SUMMARY OF THE INVENTION

One aspect of the present invention provides a method for preparing cabergoline Form I comprising dissolving cabergoline in 4-fluorotoluene and recovering the cabergoline Form 1 polymorph. Cabergoline Form I can then be obtained from the solution in 4-fluorotoluene, suitably by direct crystallization of Form I or by recovery of a solvate which can be converted to Form I.

DETAILED DESCRIPTION OF THE INVENTION

Figure 1:
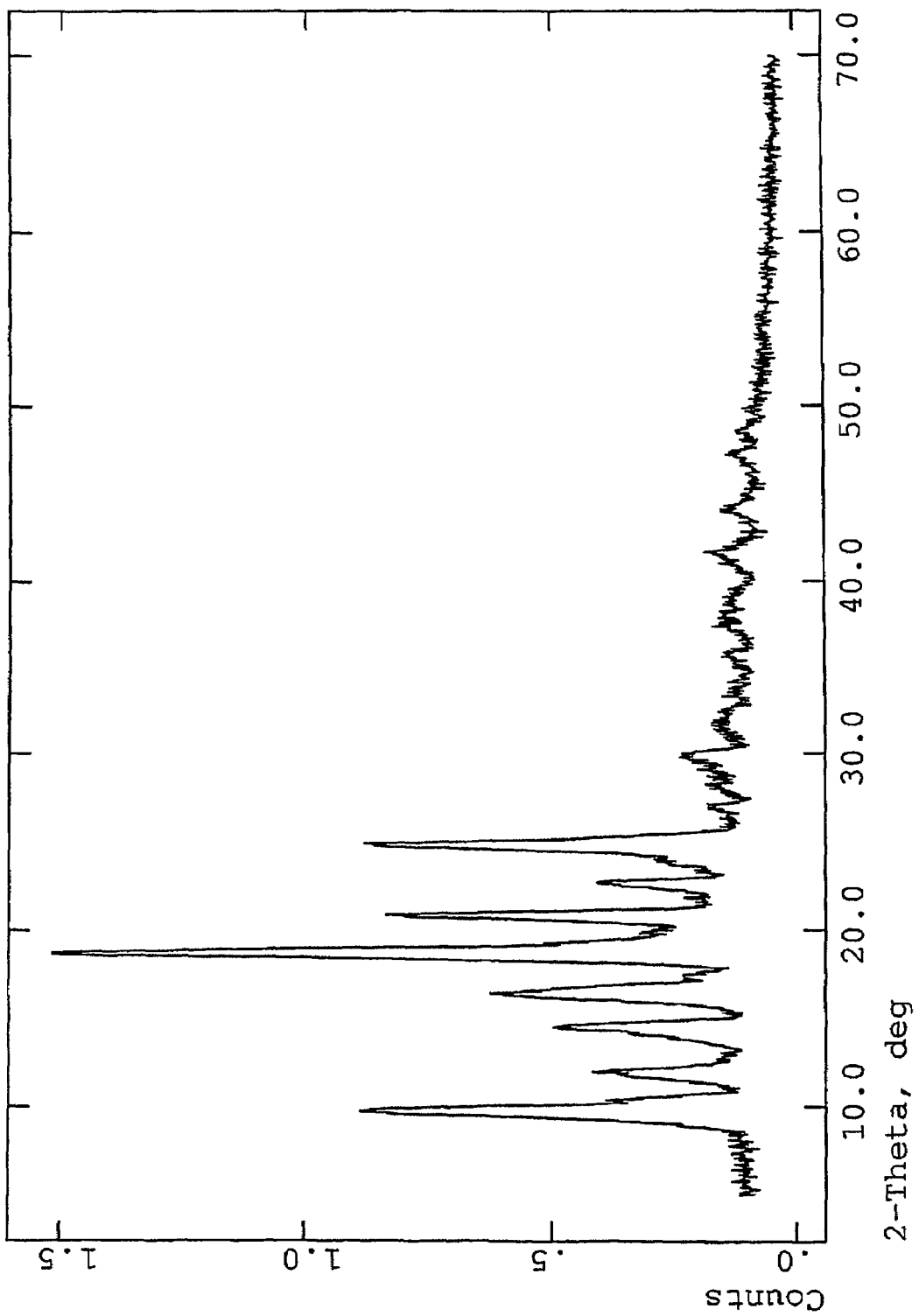
FIG. 1 is an x-ray powder diffraction pattern for the cabergoline form I of the present invention.

One embodiment of the present invention involves preparing cabergoline Form I by forming a solvate of cabergoline and 4-fluorotoluene, optionally further comprising n-heptane, and obtaining Form I cabergoline from this solvate.

Another embodiment of the present invention comprises dissolving cabergoline in a solvent comprising 4-fluorotoluene, adding heptane to form a solvate and drying the solvate to obtain Form I cabergoline.

According to a further embodiment of the present invention, a method of preparing cabergoline Form I comprising dissolving cabergoline in 1,3,5-trimethylbenzene (mesitylene) and recovering the cabergoline Form 1 polymorph. Cabergoline Form I can then be obtained from the solution in 1,3,5-trimethylbenzene, suitably by direct crystallization to obtain cabergoline Form I or by recovery of a solvate which can be converted to Form I.

In one preferred embodiment of the present invention, cabergoline Form I is prepared by forming a solvate of cabergoline and 1,3,5-trimethylbenzene, optionally adding an antisolvent comprising n-heptane to obtain the solvate, and obtaining Form I cabergoline from this solvate.

Another embodiment of the invention comprises dissolving cabergoline in a solvent comprising 1,3,5-trimethylbenzene, adding heptane to form a solvate and drying the solvate to obtain Form I cabergoline.

In yet another embodiment of the present invention, cabergoline is dissolved in a solvent which comprises 4-fluorotoluene or 1,3,5-trimethylbenzene and the solution cooled to a temperature of −5° C. or below. The solvent preferably comprises at least 75% by volume 4-fluorotoluene. It is contemplated in accordance with the present invention that the solvent may consist solely of 4-fluorotoluene. According to another aspect of the invention, the solvent preferably comprises at least 75% by volume 1,3,5-trimethylbenzene. Furthermore, it is also contemplated in accordance with the present invention that the solvent may consist solely of 1,3,5-trimethylbenzene.

Also provided by the present invention is Form I cabergoline, obtained by the methods of the invention, a solvate form of cabergoline comprising cabergoline and 4-fluorotoluene, and a solvate form of cabergoline comprising cabergoline and 1,3,5-trimethylbenzene.

In another embodiment of the present invention, cabergoline is dissolved in a solvent selected from 4-fluorotoluene and 1,3,5-trimethylbenzene. The dissolving process is optionally performed at room temperature, typically about 25-30° C. and the resulting solution is preferably filtered to remove particulate material. The temperature of the solution is then lowered to about −17° C. or below, preferably −23° C. or below, forming a precipitate of cabergoline. Formation of the cabergoline precipitate can optionally be encouraged by stirring or seeding using crystalline Form I cabergoline.

To the cabergoline precipitate an anti-solvent is added. As used herein, an anti-solvent is generally a liquid in which cabergoline, cabergoline/4-fluorotoluene solvate and/or cabergoline/1,3,5-trimethylbenzene solvate is highly insoluble. The anti-solvent preferably comprises hexane, heptane, diethylether, diisopropylether, tertiarybutylmethyl ether or mixtures of these solvents. The anti-solvent more preferably comprises heptane, and most preferably comprises n-heptane.

The addition of the anti-solvent results in formation and precipitation of cabergoline, a cabergoline/4-fluorotoluene solvate, or a cabergoline/1,3,5-trimethylbenzene solvate, forming a slurry that can be filtered to recover solid, which is optionally washed, for example with further anti-solvent, and then dried to yield cabergoline Form I having high purity.

The ratio of the first solvent, i.e., the solvent comprising 4-fluorotoluene or 1,3,5-trimethylbenzene to the second solvent, i.e., the anti-solvent, is generally in the range of 4-10:5-20 volumes, preferably in the range of 5-7:8-15 volumes and more preferably in the range of 5-7:10-12 volumes. It is most preferable that the ratio of the first solvent to the second solvent is approximately 5-6:11.

The above methods have been found, advantageously, to yield Form I cabergoline having a relatively small particle size, typically with a volume mean diameter (VMD) of less than 90 microns. Any milling of the product after crystallization tends to result in loss of polymorph purity, and therefore this relatively small particle size is a significant advantage in preparation of a pharmaceutical product having Form I cabergoline of small particle size in high purity.

Advantageously, wet solvate of the present invention that has been recovered by filtration can be rapidly dried to form crystals of Form I cabergoline. Drying can be achieved in a number of different ways. For example, drying has been carried out under reduced pressure, at pressures of 900 mbar or less, 800 mbar or less and 700 mbar or less. In each of these examples, a dried, pure Form I cabergoline was obtained within 30 hours.

Drying can also be carried out at elevated temperatures. It is contemplated in accordance with the present invention that the wet solvate can be rapidly dried at 40° C. to 60° C.

Yet another option is to dry the wet solvate in an inert gas atmosphere. The inert gas atmosphere comprises nitrogen, argon and/or other inert gases at a concentration of 80% or higher by volume. In addition, a nitrogen or other inert gas blanket can be used to dry the wet solvate or drying can be carried out in a stream of an inert gas. It has been found that drying using an inert gas can be completed in less than approximately 20 hours. This is especially an advantage when preparing Form I cabergoline at large scale.

The following examples illustrate the invention without intending to limit the scope of the invention.

EXAMPLES

Example 1

Preparation of Form I Cabergoline 5.0 grams of cabergoline (purity 99.9% by HPLC percentage peak area) was dissolved in 3 volumes of a solvent (4-fluorotoluene) to form a solution. The solution was cooled to −20° C. to give a gel. After 7 hours, 22 volumes of a pre-filtered solution of an anti-solvent (n-heptane), also at −20° C., was added dropwise over a 20-minute period.

Once the addition was complete, the slurry was stirred at −20 to −15° C. for 3.5 hours. The product was then collected by filtration under a blanket of nitrogen and the filter cake washed with cold (−20 to −15° C.) n-heptane. The filter cake was then dried under a blanket of nitrogen for 30 minutes.

The resulting solid was then placed in a vacuum oven with a nitrogen purge at 45-50° C. Full vacuum was then applied to the solid in the vacuum oven at 40 to 50° C. until the sample was at constant weight.

Samples of the product were subjected to chromatographic tests such as DRIFT IR, DSC and X-ray crystallographic analysis (as set forth in FIG. 1) and determined to be pure Form I cabergoline. The yield was 96.7%.

Example 2

The procedure of Example 1 was repeated; except that 2.0 grams of cabergoline were dissolved in 5 volumes of 4-fluorotoluene and 11 volumes of n-heptane were added in the subsequent stage.

Samples of the product were subjected to DRIFT IR and determined to be pure Form I cabergoline. DSC analysis of damp material showed a peak at 52.5° C. and DSC analysis of dry material showed a peak at 104.16° C. The yield was 77.8%.

Example 3

The procedure of Example 1 was repeated; except that 2.0 grams of cabergoline were dissolved in 3 volumes of 4-fluorotoluene and 22 volumes of n-heptane were added in the subsequent stage.

Samples of the product were subjected to DRIFT IR, DSC and X-ray crystallographic analysis and determined to be pure Form I cabergoline. DSC analysis of damp material showed a peak at 52.5° C. and DSC analysis of dry material showed a peak at 104.16° C. The yield was 82%.

Example 4

The procedure of Example 1 was repeated using 1,3,5-trimethylbenzene (mesitylene) as the solvent. Specifically, 2.0 grams of cabergoline was dissolved in 25 volumes of 1,3,5-trimethylbenzene and the resulting solution was processed as described in Example 1.

Analysis of the resulting product showed that it consisted predominantly of Form I cabergoline, together with a minor amount (3.8%) of the Form II.

Accordingly, the present invention provides methods for obtaining crystalline Form I cabergoline with high purity, which is easy to dry from the intermediate solvate and which has a particle size that facilitates preparation of a pharmaceutical product with reduced post-crystallization processing.* * * * *

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of preparing cabergoline Form I, comprising forming a solvate including cabergoline and 4-fluorotoluene and obtaining cabergoline Form I from the solvate.

2. The method of claim 1, wherein the cabergoline Form I is obtained from the solvate by drying.

3. The method of claim 2, wherein the drying is performed at a pressure of 900 mbar or less.

4. The method of claim 2, wherein the drying occurs at a temperature of at least about 40° C.

5. The method of claim 2, wherein the drying occurs in an inert gas atmosphere.

6. The method of claim 5, wherein the inert gas is selected from the group consisting of nitrogen gas and argon gas.

7. The method of claim 5, wherein the inert gas atmosphere comprises a gas mixture including at least about 80% inert gas.

8. The method of claim 7, wherein the gas mixture comprises nitrogen gas.

9. The method of claim 7, wherein the gas mixture comprises argon gas.

10. The method of claim 1, wherein the solvate is formed by dissolving cabergoline in a solvent comprising at least 75% by volume 4-fluorotoluene.

11. The method of claim 10, wherein the solvent consists of 4-fluorotoluene.

12. The method of claim 1, wherein the solvate is formed by dissolving cabergoline in a solvent comprising 4-fluorotoluene and cooling the resulting solution to a temperature of at most about −5° C.

13. The method of claim 1, further comprising the step of adding an anti-solvent to form the solvate.

14. The method of claim 13, wherein the anti-solvent is selected from the group consisting of hexane, heptane, diethylether, diisopropylether, tertiarybutylmethyl ether, and mixtures thereof.

15. The method of claim 14, wherein the anti-solvent is heptane.

16. The method of claim 15, wherein the anti-solvent is n-heptane.

17. A solvate form of cabergoline comprising cabergoline and 4-fluorotoluene.

18. The solvate form of claim 17, further comprising n-heptane.

19. A method of preparing cabergoline Form I comprising dissolving cabergoline in a first solvent comprising 4-fluorotoluene to form a solution and obtaining cabergoline Form I from the solution.

20. The method of claim 19, wherein the first solvent comprises at least 75% by volume 4-fluorotoluene.

21. The method of claim 20, wherein the first solvent consists of 4-fluorotoluene.

22. The method of claim 19, wherein the solution is cooled to a temperature of at most about −5° C.

23. The method of claim 19, further comprising the step of adding a second solvent to the solution.

24. The method of claim 23, wherein the second solvent is selected from the group consisting of hexane, heptane, diethylether, diisopropylether, tertiarybutylmethyl ether, and mixtures thereof.

25. The method of claim 24, wherein the second solvent is heptane.

26. The method of claim 25, wherein the second solvent is n-heptane.

27. The method of claim 19, further comprising the step of drying the solution to obtain cabergoline Form I.

28. The method of claim 27, wherein the drying is performed at a pressure of 900 mbar or less.

29. The method of claim 27, wherein the drying occurs at a temperature of at least about 40° C.

30. The method of claim 27, wherein the drying occurs in an inert gas atmosphere.

31. The method of claim 30, wherein the inert gas is selected from the group consisting of nitrogen gas and argon gas.

32. The method of claim 30, wherein the inert gas atmosphere comprises a gas mixture including at least about 80% inert gas.

33. The method of claim 32, wherein the gas mixture comprises nitrogen gas.

34. The method of claim 32, wherein the gas mixture comprises argon gas.

35. A method of preparing cabergoline Form I, comprising forming a solvate including cabergoline and 1,3,5-trimethylbenzene and obtaining cabergoline Form I from the solvate.

36. The method of claim 35, wherein the cabergoline Form I is obtained from the solvate by drying.

37. The method of claim 36, wherein the drying is performed at a pressure of 900 mbar or less.

38. The method of claim 36, wherein the drying occurs at a temperature of at least about 40° C.

39. The method of claim 36, wherein the drying occurs in an inert gas atmosphere.

40. The method of claim 39, wherein the inert gas is selected from the group consisting of nitrogen gas and argon gas.

41. The method of claim 39, wherein the inert gas atmosphere comprises a gas mixture including at least about 80% inert gas.

42. The method of claim 41, wherein the gas mixture comprises nitrogen gas.

43. The method of claim 41, wherein the gas mixture comprises argon gas.

44. The method of claim 35, wherein the solvate is formed by dissolving cabergoline in a solvent comprising at least 75% by volume 1,3,5-trimethylbenzene.

45. The method of claim 44, wherein the solvent consists of 1,3,5-trimethylbenzene.

46. The method of claim 35, wherein the solvate is formed by dissolving cabergoline in a solvent comprising 1,3,5-trimethylbenzene and cooling the resulting solution to a temperature of at most about −5° C.

47. The method of claim 35, further comprising the step of adding an anti-solvent to form the solvate.

48. The method of claim 47, wherein the anti-solvent is selected from the group consisting of hexane, heptane, diethylether, diisopropylether, tertiarybutylmethyl ether, and mixtures thereof.

49. The method of claim 48, wherein the anti-solvent is heptane.

50. The method of claim 49, wherein the anti-solvent is n-heptane.

51. A solvate form of cabergoline comprising cabergoline and 1,3,5-trimethylbenzene.

52. The solvate form of claim 51, further comprising n-heptane.

53. A method of preparing cabergoline Form I comprising dissolving cabergoline in a first solvent comprising 1,3,5-trimethylbenzene to form a solution and obtaining Form I cabergoline from the solution.

54. The method of claim 53, wherein the first solvent comprises at least 75% by volume 1,3,5-trimethylbenzene.

55. The method of claim 54, wherein the first solvent consists of 1,3,5-trimethylbenzene.

56. The method of claim 53, wherein the solution is cooled to a temperature of at most about −5° C.

57. The method of claim 53, further comprising the step of adding a second solvent to the solution.

58. The method of claim 57, wherein the second solvent is selected from the group consisting of hexane, heptane, diethylether, diisopropylether, tertiarybutylmethyl ether, and mixtures thereof.

59. The method of claim 58, wherein the second solvent is heptane.

60. The method of claim 59, wherein the second solvent is n-heptane.

61. The method of claim 53, further comprising the step of drying the solution to obtain cabergoline Form I.

62. The method of claim 61, wherein the drying is performed at a pressure of 900 mbar or less.

63. The method of claim 61, wherein the drying occurs at a temperature of at least about 40° C.

64. The method of claim 61, wherein the drying occurs in an inert gas atmosphere.

65. The method of claim 64, wherein the inert gas is selected from the group consisting of nitrogen gas and argon gas.

66. The method of claim 64, wherein the inert gas atmosphere comprises a gas mixture including at least about 80% inert gas.

67. The method of claim 66, wherein the gas mixture comprises nitrogen gas.

68. The method of claim 66, wherein the gas mixture comprises argon gas.

* * * * *